US009414741B2

(12) United States Patent
Yamamoto

(10) Patent No.: US 9,414,741 B2
(45) Date of Patent: Aug. 16, 2016

(54) ENDOSCOPIC DIAGNOSIS SYSTEM

(71) Applicant: FUJIFILM CORPORATION, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 444 days.

(21) Appl. No.: 13/928,059

(22) Filed: Jun. 26, 2013

(65) Prior Publication Data
US 2013/0289373 A1    Oct. 31, 2013

Related U.S. Application Data

(63) Continuation of application No. PCT/JP2011/069632, filed on Aug. 30, 2011.

(30) Foreign Application Priority Data

Dec. 27, 2010  (JP) .................... 2010-289626

(51) Int. Cl.
*A61B 5/1455* (2006.01)
*A61B 1/06* (2006.01)
*A61B 5/1459* (2006.01)
*A61B 5/155* (2006.01)
*A61B 1/00* (2006.01)

(52) U.S. Cl.
CPC ........... *A61B 1/0638* (2013.01); *A61B 1/00009* (2013.01); *A61B 5/1459* (2013.01); *A61B 5/14551* (2013.01); *A61B 1/0005* (2013.01); *A61B 1/063* (2013.01); *A61B 1/0653* (2013.01); *A61B 5/155* (2013.01)

(58) Field of Classification Search
CPC ..................................................... A61B 5/1455
See application file for complete search history.

(56) References Cited

U.S. PATENT DOCUMENTS

2011/0077462 A1*  3/2011  Saitou et al. .................. 600/109

FOREIGN PATENT DOCUMENTS

JP              64-43228 A       2/1989

* cited by examiner

*Primary Examiner* — Eric Winakur
*Assistant Examiner* — Marjan Fardanesh
(74) *Attorney, Agent, or Firm* — Birch, Stewart, Kolasch & Birch, LLP

(57) ABSTRACT

The endoscopic diagnosis system comprises an image sensor that receives reflected light from a subject illuminated with white light and first narrowband light to acquire a narrowband light image for blood vessel observation in a narrowband light observation mode, and receives reflected light from the subject illuminated with second narrowband light to acquire a narrowband light image for oxygen saturation level observation in an oxygen saturation level observation mode; a controller that controls such that the narrowband light images for blood vessel observation and oxygen saturation level observation are acquired alternately; an image processor that generates an oxygen saturation level image based on the narrowband light images for blood vessel observation and oxygen saturation level observation; and a display unit that simultaneously displays the narrowband light image for blood vessel observation and the oxygen saturation level image.

15 Claims, 10 Drawing Sheets

ENDOSCOPIC DIAGNOSIS SYSTEM

CROSS REFERENCE TO RELATED APPLICATIONS

This application is a Continuation of PCT International Application No. PCT/JP2011/069632 filed on Aug. 30, 2011, which claims priority under 35 U.S.C. 119(a) to Application No. 2010-289626 filed in Japan on Dec. 27, 2010, all of which are hereby expressly incorporated by reference into the present application.

BACKGROUND OF THE INVENTION

The present invention relates to an endoscopic diagnosis system for simultaneously acquiring and displaying a narrowband light image for blood vessel observation and a narrowband light image for oxygen saturation level observation as special light observation.

There is conventionally used an endoscope device wherein white light (normal light) emitted from a light source device is guided to the tip of an endoscope to illuminate a region under observation of a subject, and the reflected light is imaged to acquire a normal light image (white light image) in order to perform normal light observation (white light observation). In recent years, however, there is used an endoscope device wherein a region under observation of a subject is illuminated with narrowband light (special light) having a given wavelength range, and the reflected light or the like is imaged to acquire a special light image in order to perform special light observation in addition to normal light observation.

An endoscope device capable of special light observation can readily visualize biological information which is unobtainable from a normal observation image, for example, the fine structure of a new blood vessel formed in a mucosa layer or a submucosal layer in a subject's lumen and an enhanced site of lesion. When, for example, the site to be observed is a cancer-affected region, illuminating a mucosa tissue with blue narrowband light enables observation of the states of fine blood vessels and the fine structure in the superficial layer of a tissue in greater detail and thus permits diagnosis of a site of lesion with an increased accuracy.

In endoscopic observation, by switching among, for example, a normal light image, an image of blood vessel arrangement (narrowband light image for blood vessel observation) and an oxygen saturation level image of an affected region/blood vessel on a display to compare, diagnostic performance on the affected region can be effectively improved. JP 1-43228 A discloses an electronic endoscope device which switches between, for example, a normal light image and an image of blood vessel arrangement or between a normal light image and an oxygen saturation level image on a display, using an image sensor such as a CCD (Charge Coupled Device) having a color separation filter in combination with a rotary filter having different separation/transmission characteristics from the color separation filter.

First, the electronic endoscope device disclosed in JP 1-43228 A which switches between a normal light image and an image of blood vessel arrangement on a display is described below with reference to a conceptual view illustrated in FIG. 13.

When observing a normal light image, in light having wavelength range of visible light range to infrared light range emitted from a lamp, light having wavelength range of the infrared light range is cut off by an infrared cut filter, and light in the visible light range only illuminates a subject. The light reflected on the subject is then separated into colors of cyan, green and yellow at a time by an image sensor having a color filter with spectral transmission characteristics that transmits cyan (Cy) light, green (G) light, yellow (Ye) light and infrared (IR) light, respectively, and is imaged. The process generates a video signal of a normal light image (color display).

When observing an image of blood vessel arrangement, light having wavelength range from visible light range to infrared light range emitted from a lamp is sequentially turned, by a rotary filter, into light in three wavelength ranges IR1, IR2 and IR3, into which the infrared light range is divided, and the subject is sequentially illuminated with light of the respective wavelength ranges. The light reflected on the subject is then sequentially imaged by the image sensor and is synthesized, while the IR1, IR2 and IR3 wavelength ranges are assigned to the respective channels Bch, Gch and Rch corresponding to blue (B), green (G) and red (R). The process generates a video signal of an image of blood vessel arrangement (pseudo-color display).

Next, with reference to a conceptual diagram shown in FIG. 14, the electronic endoscope device disclosed by JP 1-43228 A is described, in which a normal light image and an oxygen saturation level image are switched to one another to be displayed.

The operation for observing a normal light image is same as that of the electronic endoscope device in which a normal light image and an image of blood vessel arrangement are switched to one another to be displayed.

When observing an oxygen saturation level image, light in the visible light range emitted from a lamp is sequentially turned, by a rotary filter, into light in three wavelength ranges G1, G2 and G3, into which the green light range is divided, and the subject is sequentially illuminated with light in the respective wavelength ranges. The light reflected on the subject is then sequentially imaged by the image sensor and is synthesized, while the G1, G2 and G3 wavelength ranges are each assigned to the channels Bch, Gch and Rch corresponding to B, G and R. The process generates a video signal of an oxygen saturation level image (pseudo-color display).

SUMMARY OF THE INVENTION

According to the method of JP 1-43228 A, in order to switch between a normal light image and an image of blood vessel arrangement or between a normal light image and an oxygen saturation level image, a rotary filter must be changed, so a normal light image and an image of blood vessel arrangement or a normal light image and an oxygen saturation level image cannot be simultaneously acquired and displayed. In addition, since an image of blood vessel arrangement and an oxygen saturation level image are acquired by different devices, an image of blood vessel arrangement and an oxygen saturation level image cannot be displayed at a time.

Moreover, in the method according to JP 1-43228 A, since an image of blood vessel arrangement is acquired by using infrared light, there are problems such as that the method can observe only submucosal blood vessels and cannot observe superficial blood vessels which are important for diagnosis of a site of lesion.

An object of the present invention is to provide an endoscopic diagnosis system which can acquire and display a narrowband light image for blood vessel observation capable of observing blood vessels lying in the superficial to intermediate layer and an oxygen saturation level image, and in addition a normal light image at a time.

In order to attain the object, the present invention provides an endoscopic diagnosis system, comprising:

a white light source for emitting white light;

a first narrowband light source for emitting first narrowband light having a given wavelength range;

a second narrowband light source for emitting second narrowband light having a wavelength range different from that of the first narrowband light;

a light source controller for controlling on-off actions and light amounts of the white light source, the first narrowband light source and the second narrowband light source, respectively;

an image sensor for receiving reflected light from a subject illuminated with the white light to acquire a normal light image in a normal light observation mode, receiving reflected light from the subject illuminated with the white light and the first narrowband light emitted at a first emission ratio toward the subject to acquire a narrowband light image for blood vessel observation in a narrowband light observation mode, and receiving reflected light from the subject illuminated with the second narrowband light emitted toward the subject to acquire a narrowband light image for oxygen saturation level observation in an oxygen saturation level observation mode;

a controller for switching between the narrowband light observation mode and the oxygen saturation level observation mode alternately in this order to control such that the narrowband light image for blood vessel observation and the narrowband light image for oxygen saturation level observation are acquired alternately in a time-sharing manner;

an image processor for calculating an oxygen saturation level of blood hemoglobin of the subject based on the narrowband light image for blood vessel observation and the narrowband light image for oxygen saturation level observation to generate an oxygen saturation level image showing a distribution of the oxygen saturation level; and a display unit for simultaneously displaying the narrowband light image for blood vessel observation and the oxygen saturation level image.

Preferably, in the narrowband light observation mode, the image processor is adapted to generate a synthesized image in which the narrowband light image for blood vessel observation and the oxygen saturation level observation image are superposed, and the display unit is adapted to display the synthesized image.

Preferably, in the narrowband light observation mode, the image processor is adapted to generate a synthesized image in which the narrowband light image for blood vessel observation and the oxygen saturation level image are laid out, and the display unit is adapted to display the synthesized image.

Preferably, the light source controller is adapted to control such that, a first illumination mode and a second illumination mode are switched alternately in the narrowband light observation mode, the white light and the first narrowband light being emitted to illuminate the subject at the first emission ratio in the first illumination mode, and the first narrowband light being emitted to illuminate the subject at the second emission ratio at which an emission amount of the first narrowband light is so reduced that an effect of the first narrowband light on the narrowband light image for blood vessel observation is ignorable in the second illumination mode, and the image sensor is adapted to acquire the narrowband light image for blood vessel observation in the first illumination mode and the normal light image in the second illumination mode alternately in the narrowband light observation mode.

Preferably, in the narrowband light observation mode, the image processor is adapted to generate a synthesized image in which the normal light image, the narrowband light image for blood vessel observation and the oxygen saturation level image are superposed, and the display unit is adapted to display the synthesized image.

Preferably, in the narrowband light observation mode, the image processor is adapted to generate a synthesized image in which the narrowband light image for blood vessel observation and the oxygen saturation level image are superposed, and the display unit is adapted to display the normal light image and the synthesized image as being laid out.

Preferably, in the narrowband light observation mode, the image processor is adapted to generate a synthesized image in which the normal light image, the narrowband light image for blood vessel observation and the oxygen saturation level image are laid out, and the display unit is adapted to display the synthesized image.

Preferably, the first narrowband light has a wavelength range of 405 nm±10 nm, and the second narrowband light has a wavelength range of 473 nm±10 nm.

Preferably, the white light source comprises a third narrowband light source for emitting third narrowband light having a given wavelength range and a fluorescent body which is excited to emit luminescent light when illuminated with the third narrowband light, so that the third narrowband light is combined with the luminescent light to generate pseudo white light.

Preferably, the third narrowband light has a wavelength range of 445 nm±10 nm.

According to the present invention, a narrowband light image for blood vessel observation and a narrowband light image for oxygen saturation level observation are simultaneously acquired in a time-sharing manner and therefore the narrowband light image for blood vessel observation and the oxygen saturation level image can be displayed at a time. In addition, in the narrowband light observation mode, the subject is illuminated with white light and narrowband light at a given emission ratio to acquire a narrowband light image for blood vessel observation and therefore blood vessels lying in the superficial to intermediate layer of the subject can be observed.

Furthermore, by alternately switching between the narrowband light observation mode and the oxygen saturation level observation mode in this order, an image signal of the narrowband light image for blood vessel observation acquired in the narrowband light observation mode can be used for calculation of the oxygen saturation level. Hence, an endoscopic image required to calculate the oxygen saturation level can be obtained by only taking a narrowband light image for oxygen saturation level observation. In this manner, the accuracy of a motion picture can be improved when observing a plurality of endoscopic images at a time.

DETAILED DESCRIPTION OF THE INVENTION

The endoscopic diagnosis system according to the present invention will be described in detail based on the preferred embodiments illustrated in the attached drawings.

Figure 1:
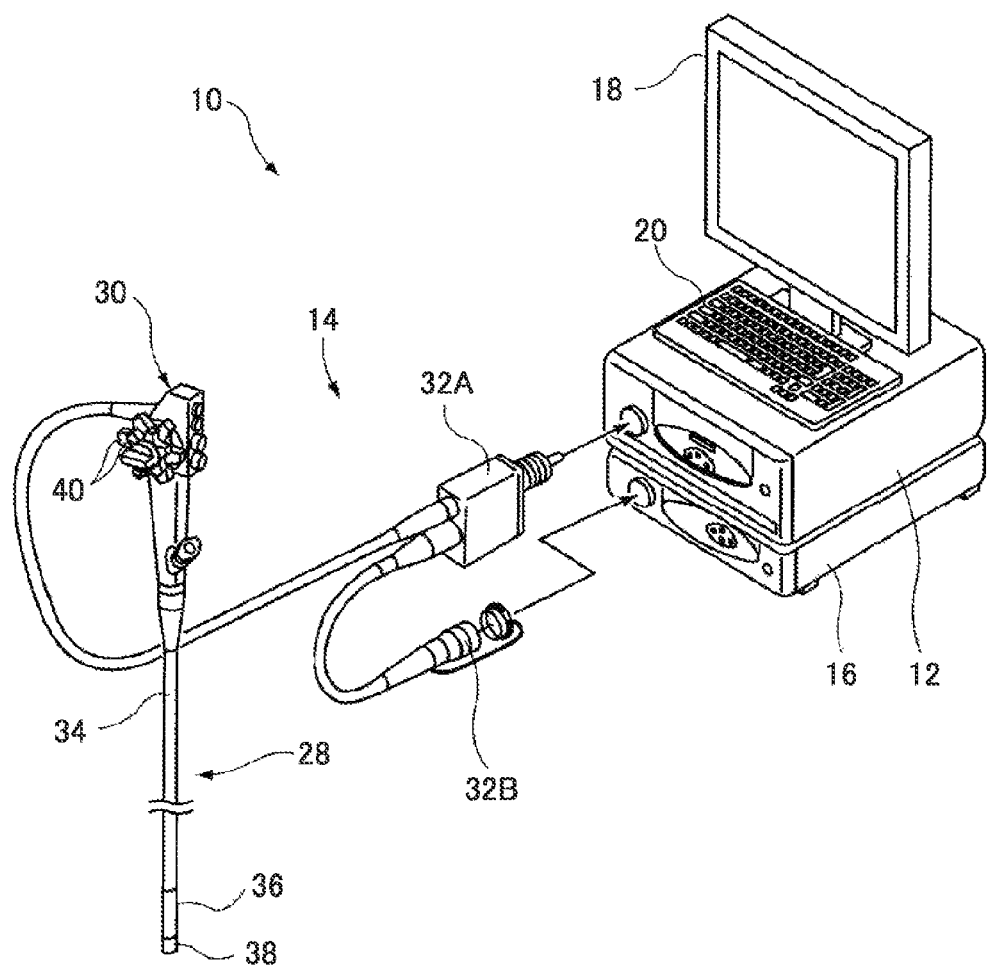
FIG. 1 is an external view of an embodiment illustrating a configuration of the endoscopic diagnosis system according to the invention.
Figure 2:
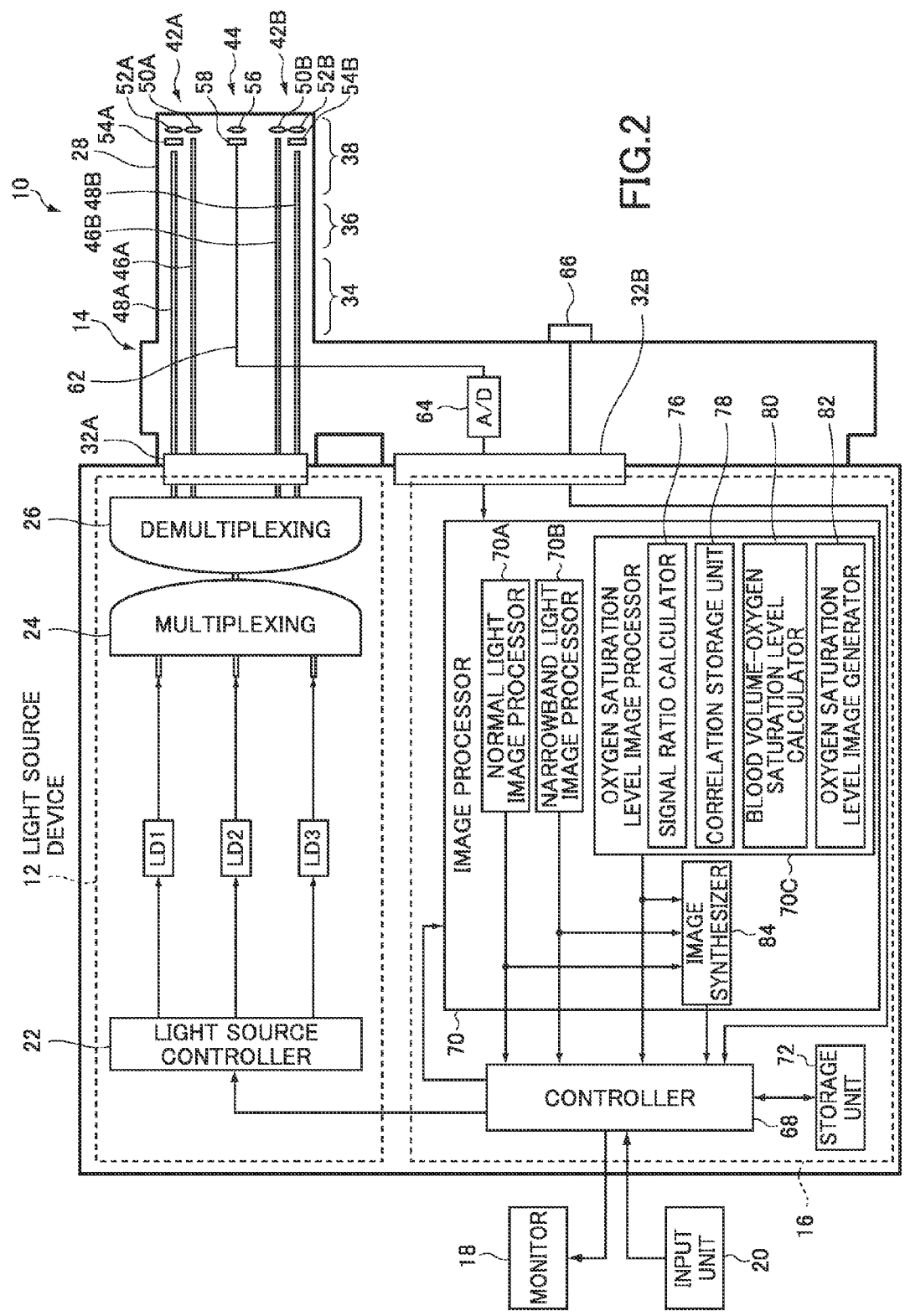
FIG. 2 is a block diagram illustrating an internal configuration of the endoscopic diagnosis system of FIG. 1.

FIG. 1 is an external view of an embodiment illustrating a configuration of the endoscopic diagnosis system according to the invention, and FIG. 2 is a block diagram illustrating an internal configuration thereof. An endoscopic diagnosis system 10 illustrated in these figures comprises a light source device 12 for emitting light having different ranges of wavelength, an endoscope device 14 for guiding the light emitted from the light source device 12 to illuminate a subject's region under observation with illumination light and imaging reflected light from the subject, a processor 16 for image-processing an acquired image acquired by the endoscope device 14 and outputting an endoscopic image, a display unit 18 for displaying the endoscopic image outputted from the processor 16, and an input unit 20 for receiving input operations.

The endoscopic diagnosis system 10 has a normal light observation mode for illuminating the subject with normal light and imaging the reflected light thereof to display (observe) a normal light image, and a special light observation mode (narrowband light observation mode and oxygen saturation level observation mode) for illuminating the subject with special light and imaging the reflected light thereof to display a special light image (a narrowband light image for blood vessel observation and an oxygen saturation level image). The observation modes are switched as appropriate from one to another according to an instruction entered by a selector switch 66 of the endoscope device 14 or the input unit 20.

The light source device 12 comprises a light source controller 22, three kinds of laser light sources LD1, LD2 and LD3 for emitting laser beams having different wavelength ranges, a combiner (multiplexer) 24, and a coupler (demultiplexer) 26.

According to this embodiment, the laser light sources LD1, LD2 and LD3 emit narrowband light beams having given wavelength ranges (e.g., central wavelength +/−10 nm) with different central wavelengths of 405 nm, 445 nm and 473 nm, respectively. The laser light source LD1 is provided to acquire a narrowband light image for blood vessel observation, the laser light source LD2 is provided to acquire a normal light image by generating excitation light for normal light observation to cause a fluorescent body described later to generate white light (pseudo white light), and the laser light source LD3 is provided to acquire a narrowband light image for oxygen saturation level observation to generate an oxygen saturation level image.

A laser beam having a central wavelength of 473 nm as narrowband light for oxygen saturation level observation can be used to observe changes in the oxygen saturation level, since absorption of the laser beam having this wavelength in blood changes in accordance with the changes in the oxygen saturation level.

The white light source (normal light source) for generating white light is not limited to a light source using a combination of excitation light and a fluorescent body and may be any light source to generate white light, including, for example, a xenon lamp, a halogen lamp, and a white LED (light emitting diode). The laser beams emitted from the laser light sources LD1, LD2 and LD3 are not limited in wavelength to the above, laser beams capable of serving the same purpose may be selected as appropriate.

The on/off control and light amount control of the laser light sources LD1, LD2 and LD3 are made individually by the light source controller 22 that is controlled by a controller of the processor 16 described later, and the emission timing and the emission amount ratio of light from the laser light sources LD1, LD2 and LD3 can be freely varied.

Broad area type InGaN-based laser diodes may be used for the laser light sources LD1, LD2 and LD3, and InGaNAs-based laser diodes and GaNAs-based laser diodes may also be used.

The light source controller 22 turns the laser light source LD1 and LD3 off and turns the laser light source LD2 on in the normal light observation mode. In the special light observation mode, the light source controller 22 sequentially switches the observation mode between the narrowband light observation mode and the oxygen saturation level observation mode in this order in every frame time, for example. The switching may be made once in a plurality of frames in lieu of every frame time. The light source controller 22 turns the laser light sources LD1, LD2 on and turns the laser light source LD3 off in the narrowband light observation mode, while the light source controller 22 turns the laser light sources LD1 and LD2 off and turns the laser light source LD3 on in the oxygen saturation level observation mode.

The laser beams emitted from the laser light sources LD1, LD2 and LD3 are passed through condenser lenses (not shown) to enter their respective optical fibers, combined by the combiner 24 and divided into four channels of light beams by the coupler 26 before being transmitted to a connector unit 32A. The combiner 24 and the coupler 26 are composed of, for example, a half mirror or a reflection mirror. The configuration is not limited thereto, however, the laser beams from the laser light sources LD1, LD2 and LD3 may be directly transmitted to the connector unit 32A in lieu of through the combiner 24 and the coupler 26.

Then, the endoscope device 14 is an electronic endoscope instrument comprising an optical system for illumination for emitting four channels (four beams) of illumination light from the tip of an endoscope insertion section inserted into the inside of a subject's body, and a channel (one sensor) of optical imaging system for acquiring an endoscopic image of the region under observation. The endoscope device 14 comprises the endoscope insertion section 28, an operating unit 30 for bending the tip of the endoscope insertion section 28 and performing observation operations, and connector units 32A, 32B for detachably connecting the endoscope device 14 to the light source device 12 and the processor 16.

The endoscope insertion section 28 comprises a flexible portion 34 having flexibility, a bending portion 36, and a tip portion 38 (also referred to below as endoscope tip portion).

The bending portion 36 is provided between the flexible portion 34 and the tip portion 38 and is so configured as to be bendable by rotating an angle knob 40 provided on the operating unit 30. The bending portion 36 can be bent in any direction and to any angle according to, for example, the subject's site for which the endoscope device 14 is used, so that the endoscope tip portion 38 may be directed toward a desired site for observation.

Figure 3:
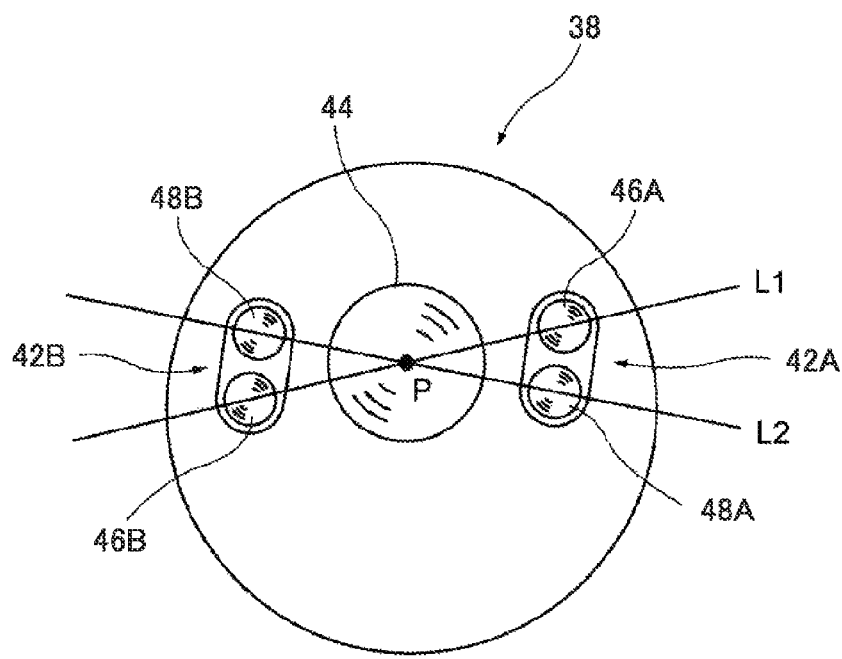
FIG. 3 is a conceptual view illustrating a tip portion of an endoscope insertion section of the endoscopic diagnosis system of FIG. 1.

At the tip end surface of the endoscope tip portion 38 are provided two channels of illumination windows 42A, 42B for illuminating a region under observation and a channel of observation window 44 for imaging the reflected light from the region under observation as illustrated in the conceptual view of FIG. 3.

On the inside of the illumination window 42A are provided two channels of optical fibers 46A, 48A. The optical fibers 46A, 48A extend from the light source device 12 through the connector unit 32A to the endoscope tip portion 38. The optical fiber 46A has at its tip portion (its end closer to the illumination window 42A) an optical system including, for example, a lens 50A. On the other hand, the optical fiber 48A has at its tip portion a fluorescent body 54A, and beyond the fluorescent body 54A is provided an optical system including, for example, a lens 52A.

On the inside of the illumination window 42B are likewise provided two channels of optical fibers: an optical fiber 46B having at its tip portion an optical system including, for example, a lens 50B, and an optical fiber 48B having at its tip portion an optical system including, for example, a fluorescent body 54B and a lens 52B.

As illustrated in FIG. 3, the illumination windows 42A, 42B are located on opposite sides of the observation window 44 in the endoscope tip portion 38. The four optical fibers 46A, 46B and 48A, 48B accommodated inside the illumination windows 42A, 42B are alternately located such that a line L2 connecting the optical fibers 48A, 48B including the fluorescent bodies 54A, 54B intersects with a line L1 connecting the optical fibers 46A, 46B including no fluorescent body at the central part P of the observation window 44. The optical fibers 46A, 46B and 48A, 48B are located in this manner, thus preventing uneven illumination.

The fluorescent bodies 54A, 54B comprise a plurality of kinds of fluorescent substances (e.g., YAG-based fluorescent substance or BAM ($BaMgAl_{10}O_{17}$)-based fluorescent substance) that emit green to yellow light when excited upon absorbing part of the blue laser beam emitted from the laser light source LD2. When the excitation light for normal light observation illuminates the fluorescent bodies 54A, 54B, the green to yellow luminescent light (fluorescence) emitted from the excited fluorescent bodies 54A, 54B are combined with part of the blue laser beam that was transmitted without being absorbed by the fluorescent bodies 54A, 54B to generate white light (pseudo white light).

Figure 4:
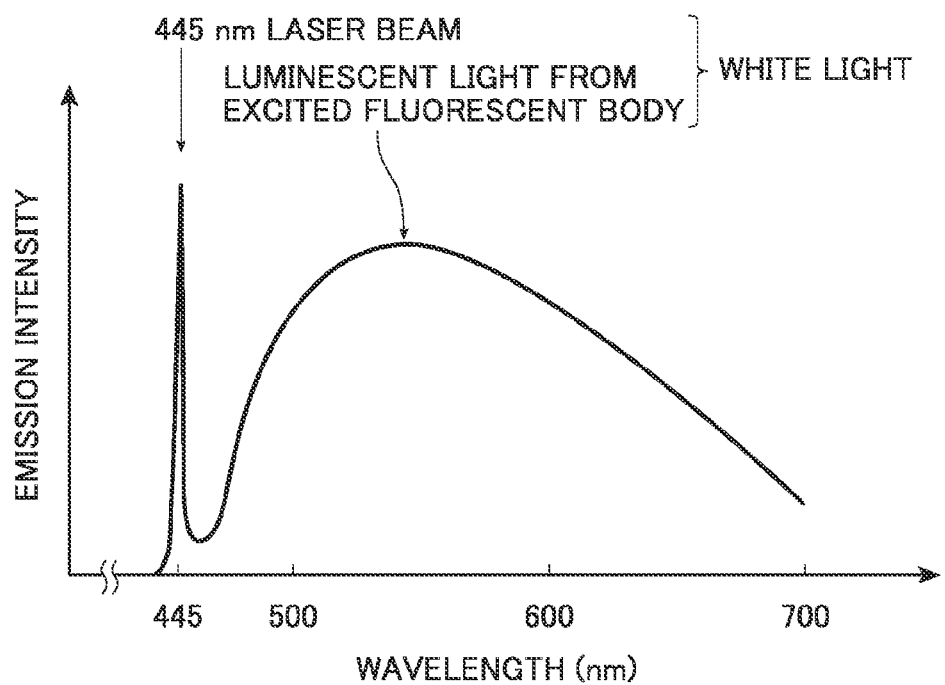
FIG. 4 is a graph illustrating an emission spectrum of a blue laser beam emitted from a blue laser light source and light obtained through wavelength conversion of the blue laser beam by a fluorescent body.

FIG. 4 is a graph illustrating an emission spectrum of the blue laser beam emitted from a blue laser light source and of light obtained through wavelength conversion of the blue laser beam by a fluorescent body. The blue laser beam emitted from the laser light source LD2 is represented by an emission line having a central wavelength of 445 nm, the luminescent light emitted from the fluorescent bodies 54A, 54B excited by the blue laser beam has a spectral intensity distribution such that the light emission intensity increases in a wavelength range of about 450 nm to about 700 nm. The luminescent light emitted by the excitation is combined with the blue laser beam to produce the pseudo white light as described above.

The white light as used in the invention is not limited to light containing strictly all the wavelength components of visible light but need only contain light having a specific wavelength range such as, for example, light having reference colors such as red, green and blue, as well as the above pseudo white light. Thus, the white light herein broadly also includes, for example, light containing wavelength components corresponding to green to red light and light containing wavelength components corresponding to blue to green light.

The optical system for illumination on the side closer to the illumination window 42A has the same configuration and operation as those of the optical system for illumination on the side close to the illumination window 42B, so that the illumination windows 42A, 42B basically emit equal illumination light simultaneously. The illumination windows 42A, 42B may emit different illumination light. Provision of optical systems for illumination that emit four channels of illumination light is not essential and, for example, an optical system for illumination to emit two channels of illumination light one including a fluorescent body and the other including no fluorescent body can also achieve the equivalent function.

In addition, when a laser beam having a central wavelength of 445 nm which is working as excitation light for normal light observation and a laser beam having a central wavelength of 405 nm which is working as the narrowband light for blood vessel observation are emitted simultaneously, the former can also be combined with the latter to illuminate the fluorescent bodies 54A, 54B.

Figure 5:
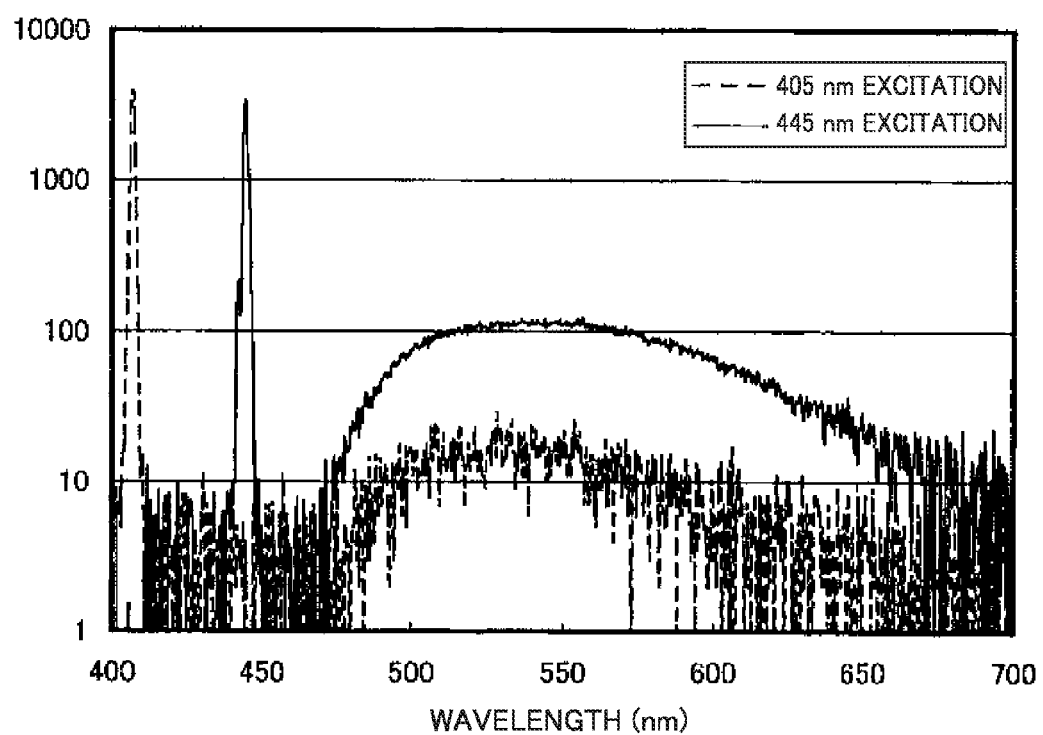
FIG. 5 is a graph illustrating emission spectra of excitation light emitted from a fluorescent body which was excited by laser beams having central wavelengths of 405 nm and 445 nm.

FIG. 5 is a graph illustrating emission spectra of excitation light emitted from a fluorescent body which was excited by laser beams having central wavelengths of 405 nm and 445 nm. In the graph, the vertical axis shows light intensity (a.u.: any unit), and the horizontal axis shows wavelength (nm). As shown in the graph, the fluorescent bodies 54A, 54B illuminated with the laser beam having a central wavelength of 405 nm emit excitation light having light intensity which is a fraction of that when illuminated with the laser beam having a central wavelength of 445 nm. Hence, even if the fluorescent bodies 54A, 54B are illuminated with the laser beam having a central wavelength of 405 nm together with the laser beam having a central wavelength of 445 nm, the laser beam having a central wavelength of 405 nm would hardly cause the fluorescent bodies 54A, 54B to be excited to emit luminescent light.

Accordingly, it is not necessary to guide the narrowband light for blood vessel observation by an optical fiber having no fluorescent body, the excitation light for normal light observation and the narrowband light for blood vessel observation can be combined and guided only by an optical fiber having a fluorescent body.

Then, on the inside of the observation window 44 is installed an optical system including, for example, an object lens unit 56 for introducing image light from the subject's region under observation, and further behind the object lens unit 56 is installed an image sensor 58 such as a CCD (Charge Coupled Device) image sensor or a CMOS (Complementary Metal-Oxide Semiconductor) image sensor for acquiring image information on the subject's region under observation.

The image sensor 58 receives light from the object lens unit 56 on a light receiving surface (imaging surface), photoelectrically converts the received light into imaging signals (analog signals), and outputs the imaging signals. The light receiving surface of the image sensor 58 is provided with red, green and blue color filters having spectral transmittances dividing a wavelength range of about 370 nm to about 720 nm of visual light into three ranges, a red pixel, a green pixel and a blue pixel forming one set of pixels, a plurality of sets of pixels are arranged in the form of matrix.

The light emitted from the light source device 12 and guided through the optical fibers 46A, 46B and 48A, 48B is emitted from the endoscope tip portion 38 toward the subject's region under observation. The region under observation illuminated with the illumination light is imaged on the light receiving surface of the image sensor 58 through the object lens unit 56, and undergoes photoelectric conversion in the image sensor 58 to obtain an image. The image sensor 58 outputs an imaging signal (analog signal) of the subject's imaged region under observation.

The imaging signal (analog signal) of an endoscopic image outputted from the image sensor 58 is inputted to an A/D converter 64 via a scope cable 62. The A/D converter 64 converts the imaging signal (analog signal) supplied from the image sensor 58 to an image signal (digital signal). The image signal obtained through the conversion passes through the connector unit 32B to enter an image processor of the processor 16.

In the normal light observation mode, the excitation light for normal light observation emitted from the light source LD2 is guided through the optical fibers 48A, 48B to illuminate the fluorescent bodies 54A, 54B, whereupon the white light generated from the fluorescent bodies 54A, 54B is emitted through the illumination windows 42A, 42B to illuminate the subject's region under observation. The reflected light from the subject's region under observation illuminated with the white light is condensed by the object lens unit 56, whereupon a normal light image is acquired by the image sensor 58.

In the narrowband light observation mode, in addition to excitation light for normal light observation, the narrowband light emitted from the laser light source LD1 is guided through the optical fibers 46A, 46B, whereupon the above-described white light and narrowband light are simultaneously emitted through the illumination windows 42A, 42B to illuminate the subject's region under observation at a given emission ratio. The reflected light from the subject's region under observation illuminated with the white light and narrowband light is condensed by the object lens unit 56, whereupon a narrowband light image for blood vessel observation is acquired by the image sensor 58.

In the oxygen saturation level observation mode, the narrowband light emitted from the laser light source LD3 is guided through the optical fibers 46A, 46B and emitted through the illumination windows 42A, 42B to illuminate the subject's region under observation. The reflected light from the subject's region under observation illuminated with the narrowband light is condensed by the object lens 56, whereupon a narrowband light image for oxygen saturation level observation is acquired by the image sensor 58.

Although not shown, the operating unit 30 and the endoscope insertion section 28 contain in their interiors various channels such as a forceps channel for inserting, for example, a tissue collecting tool and air supply/water supply channels.

Then, the processor 16 comprises the controller 68, the image processor 70, and a storage unit 72. The controller 68 is connected to the display unit 18 and the input unit 20. The processor 16 controls the light source controller 22 of the light source device 12 according to an instruction inputted from the selector switch 66 of the endoscope device 14 or the input unit 20, image-processes an image signal (image data) inputted from the endoscope device 14, produces a display image and outputs the produced display image to the display unit 18.

The controller 68 controls the operations of the image processor 70 and the light source controller 22 of the light source device 12 according to instructions given by the selector switch 66 of the endoscope device 14 and the input unit 20, such as, for example, an observation mode instruction and an image display mode instruction. The image display mode is an instruction which specifies an image display mode such as for displaying any one of a normal light image, a narrowband light image for blood vessel observation and an oxygen saturation level image, or combining two or more images (normal light image, narrowband light image for blood vessel observation, oxygen saturation level image) to display a synthesized image in which, for example, the images are superposed or laid out.

The image processor 70 performs given image processing on the image signal entered from the A/D converter 64 of the endoscope device 14 according to the observation mode and the image display mode under the control of the controller 68 depending on the kinds of images including a normal light image, a narrowband light image for blood vessel observation, an oxygen saturation level image and a synthesized image. The image signal processed by the image processor 70 is supplied to the controller 68, which produces an endoscopic observation image from the processed image signal and various kinds of information. The endoscopic observation image is displayed on the display unit 18, and where necessary, stored in the storage unit 72 composed of a memory or a storage device.

The image processor 70 comprises a normal light image processor 70A, a narrowband light image processor 70B, an oxygen saturation level image processor 70C and an image synthesizer 84.

The normal light image processor 70A, the narrowband light image processor 70B, and the oxygen saturation level image processor 70C perform given image processing suited to respective endoscopic images on the image signals of the normal light image, the narrowband light image for blood vessel observation, and the narrowband light image for oxygen saturation level observation, respectively, in the normal light observation mode, the narrowband light observation mode, and the oxygen saturation level observation mode and output (produce) a processed normal light image signal, narrowband light image signal for blood vessel observation, and narrowband light image signal for oxygen saturation level observation.

Figure 6:
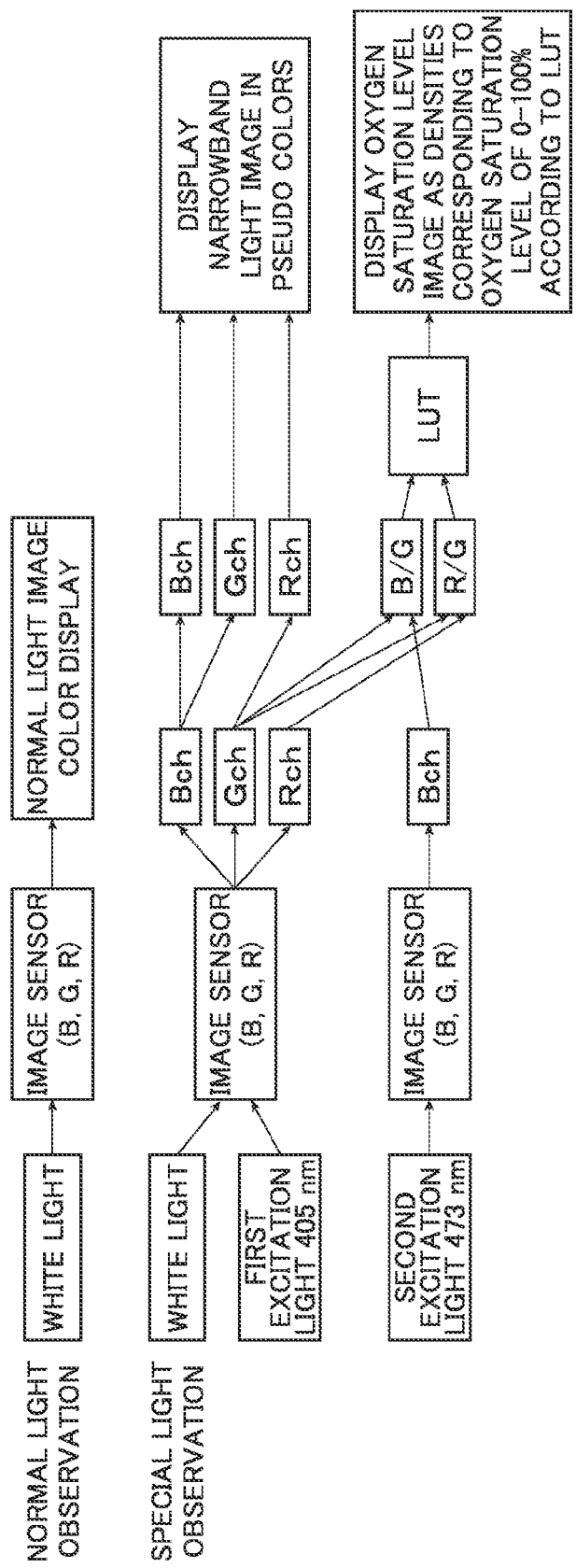
FIG. 6 is a conceptual view illustrating processing performed by the endoscopic diagnosis system of FIG. 1 in respective observation modes.

As illustrated in the conceptual view of FIG. 6, the normal light image processor 70A uses the red, the green, and the blue channels (pixels) of image data (image signals) of the normal light image to output the normal light image signals for color display of the normal light image in the normal light observation mode.

The narrowband light image processor 70B assigns the blue channel (Bch) of image data of the narrowband light image for blood vessel observation to the blue channel and the green channel (Gch) and assigns the green channel of image data to the red channel (Rch) in the narrowband light observation mode to output the narrowband light image signals for blood vessel observation for pseudo color display of the narrowband light image for blood vessel observation.

The oxygen saturation level image processor 70C calculates, in the oxygen saturation level observation mode, the oxygen saturation level of blood hemoglobin of the subject from the signal ratios B/G and R/G as well as from the LUT regarding the correlation of the blood volume and the oxygen saturation level with the signal ratios B/G and R/G to be described later, based on the image signals of the G channel and R channel of a narrowband light image for blood vessel observation and of the B channel of a narrowband light image for oxygen saturation level observation, and outputs the narrowband light image signals for oxygen saturation level observation for displaying (e.g., for pseudo color displaying) a distribution of oxygen saturation level.

As illustrated in FIG. 2, the oxygen saturation level image processor 70C comprises a signal ratio calculator 76, a correlation storage unit 78, a blood volume-oxygen saturation level calculator 80, and an oxygen saturation level image generator 82.

The signal ratio calculator 76 specifies a blood vessel region from image signals of a narrowband light image for oxygen saturation level observation based on a difference between an image signal of the blood vessel portion and an image signal of the other portion. Thereafter, the signal ratio calculator 76 obtains signal ratios B/G and R/G from image signals G and R respectively of the G channel and the R channel of the narrowband light image for blood vessel observation and from an image signal B of the B channel of the narrowband light image for oxygen saturation level observation for the pixel at the same position within the blood vessel region.

Here, B refers to an image signal of a single color illumination light having a central wavelength of 473 nm, G refers to an image signal of spectral illumination light of the luminescent light in the G color having a wavelength range of about 540 to about 580 nm emitted from the excited fluorescent bodies 54A, 54B, and R refers to an image signal of spectral illumination light of the same in the R color having a wavelength range of about 590 to about 700 nm. B and R are image signals corresponding to reflected light of two narrowband light beams in wavelength ranges where the absorbance coefficients (absorbance) of reduced hemoglobin and of oxygenated hemoglobin would reverse in magnitude in accordance with the oxygen saturation level of blood hemoglobin, while G is an image signal corresponding to reflected light of a narrowband light beam in a wavelength range where the absorbance coefficient is the same.

Figure 7:
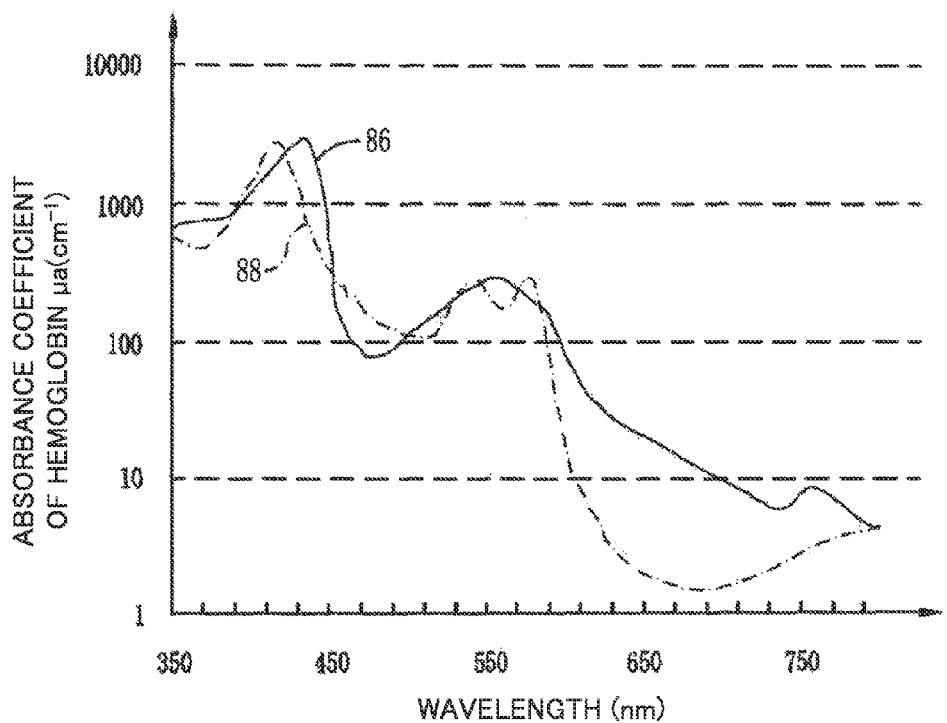
FIG. 7 is a graph illustrating absorbance coefficients of hemoglobin.
Figure 8:
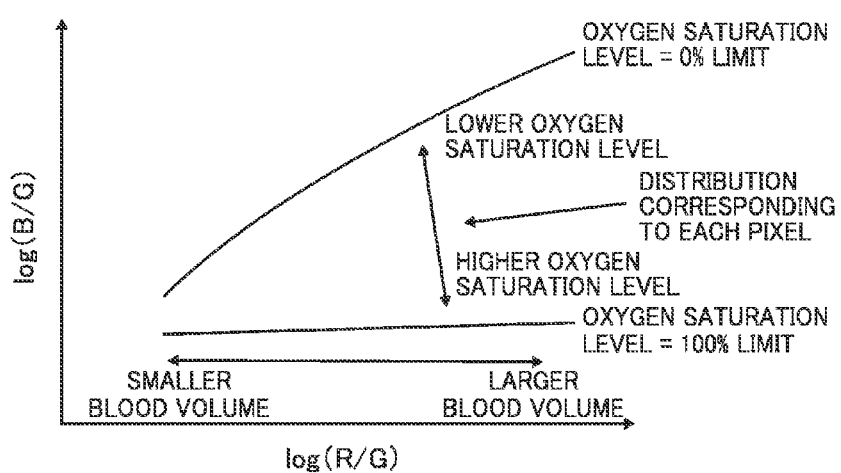
FIG. 8 is a graph illustrating the correlation of a blood volume and an oxygen saturation level with signal ratios B/G and R/G.

The correlation storage unit 78 stores a correlation of a blood volume and an oxygen saturation level with the signal ratios B/G and R/G as illustrated in FIG. 8, for example, in a form like a look-up table (LUT). The correlation is of a case where the blood vessel has the absorbance coefficient of hemoglobin shown in FIG. 7 and was obtained by analyzing a number of image signals recorded in the past optical measurements of living bodies, for example.

FIG. 7 is a graph illustrating absorbance coefficients of hemoglobin. In the graph, the vertical axis shows light absorbance coefficient $\mu a$ ($cm^{-1}$) of hemoglobin, and the horizontal axis shows wavelength (nm). As shown in the graph, the blood hemoglobin has light absorption characteristics in which the absorbance coefficient $\mu a$ varies depending on the wavelength of illuminating light. The absorbance coefficient $\mu a$ indicates an absorbance which is a magnitude of light absorption by hemoglobin. The reduced hemoglobin 86 which is not bound with oxygen and the oxygenated hemoglobin 88 which is bound with oxygen have different light absorption characteristics from each other, resulting in a difference in absorbance, except at isosbestic points (intersections between the respective hemoglobins 86 and 88 in FIG. 7) where the same absorbance (absorbance coefficient $\mu a$) is seen. In general, since the distribution shown in FIG. 7 changes non-linearly depending on the site under observation, it is necessary to preliminarily obtain the distribution through actual measurements of living tissues, light propagation simulation and the like.

FIG. 8 is a graph illustrating the correlation of a blood volume and an oxygen saturation level with signal ratios B/G and R/G. In the graph, the horizontal axis shows log (R/G), and the vertical axis shows log (B/G). As indicated in the graph, the value of the signal ratio R/G changes depending on the blood volume, thus, the larger the blood volume, the larger the value of the signal ratio R/G is. The value of the signal ratio B/G changes depending on both the blood volume and the oxygen saturation level. In other words, the larger the blood volume, the larger the value of the signal ratio B/G is, and the lower the oxygen saturation level, the larger the value of the signal ratio B/G is.

The blood volume-oxygen saturation level calculator 80 calculates a blood volume and an oxygen saturation level corresponding to the signal ratios B/G and R/G calculated by the signal ratio calculator 76 based on the correlation stored in the correlation storage unit 78.

The oxygen saturation level image generator 82 has color tables in which color information is assigned depending on the magnitude of an oxygen saturation level. The color tables can be switched to one another in accordance with an instruction inputted by the input unit 20, and one suitable for observing a particular site to be observed such as esophagus, stomach and large intestine is selected. The oxygen saturation level image generator 82 specifies the color information corresponding to the oxygen saturation level calculated in the blood volume-oxygen saturation level calculator 80 by using the color table to generate a narrowband light image signal for oxygen saturation level observation reflecting (displaying in pseudo-color) the oxygen saturation level of blood hemoglobin.

The image synthesizer 84, following the observation mode and the image display mode, generates a synthesized image by composing two or more of a normal light image, a narrowband light image for blood vessel observation and an oxygen saturation level image based on the normal light image signal, a narrowband light image signal for blood vessel observation and a narrowband light image signal for oxygen saturation level observation stored in the storage unit 72 and outputs a synthesized image signal. The image synthesizer 84 generates a synthesized image in which two or more images (a normal light image, a narrowband light image for blood vessel observation and an oxygen saturation level image) are superposed or laid out.

A normal light image signal, a narrowband light image signal for blood vessel observation, a narrowband light image signal for oxygen saturation level observation and a synthesized image signal are stored in the storage unit 72 for each image (each frame) as a unit, for example.

The image processor 70 outputs a normal light image signal, a narrowband light image signal for blood vessel observation, a narrowband light image signal for oxygen saturation level observation and a synthesized image signal, and the signals are inputted to the controller 68. The controller 68, following the observation mode and the image display mode, displays any of a normal light image, a narrowband light image for blood vessel observation, an oxygen saturation level image and a synthesized image on the display unit 18, based on the normal light image signal, the narrowband light image signal for blood vessel observation, the narrowband light image signal for oxygen saturation level observation and the synthesized image signal.

Figure 9:
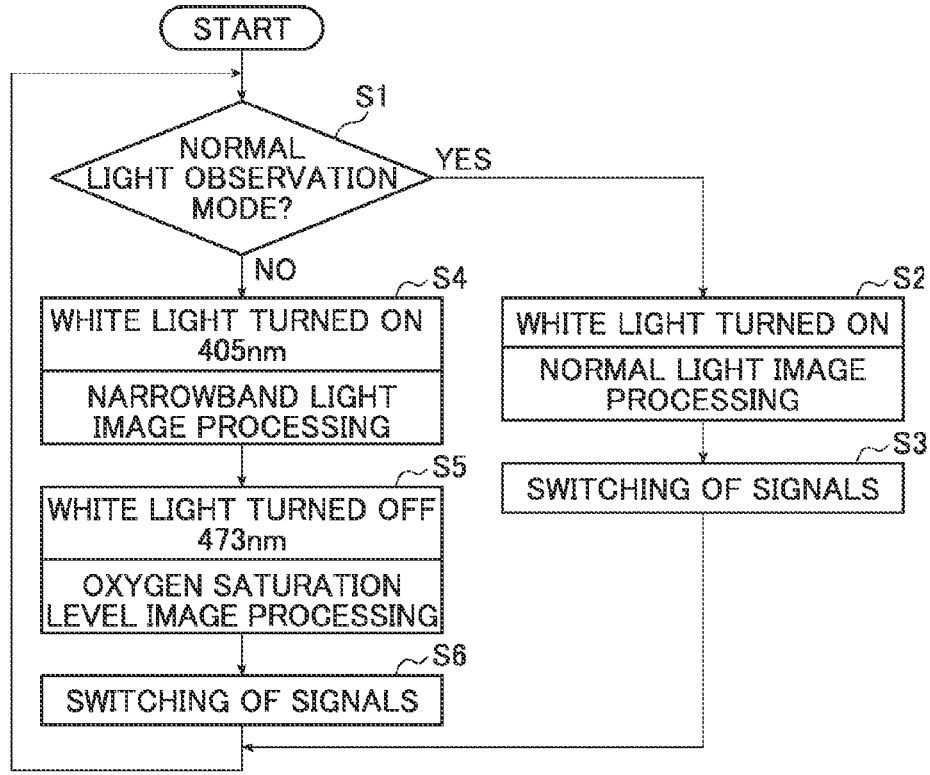
FIG. 9 is a flow chart illustrating an example of operation of the endoscopic diagnosis system of FIG. 1.

Next, the operation of the endoscopic diagnosis system 10 will now be described referring to the flowchart of FIG. 9.

First, the controller 68 judges whether the observation mode is the normal light observation mode (step S1).

When the observation mode is judged to be the normal light observation mode in step S1 (YES in step S1), the laser light sources LD1 and LD3 are turned off while the laser light source LD2 is turned on, and two channels of excitation light for normal light observation (laser beam having a central wavelength of 445 nm) are emitted from the light source device 12 (step S2).

In the endoscope device 14, the excitation light for normal light observation is guided by the optical fibers 48A, 48B to illuminate the fluorescent bodies 54A, 54B, and the white light emitted from the fluorescent bodies 54A, 54B illuminates the subject in the normal light observation mode. The reflected light from the subject illuminated with the white light is imaged by the image sensor 58, and the A/D converter 64 outputs the image signal of the normal light image.

According to the observation mode, in the processor 16, the image signal of the normal light image is inputted to the normal light image processor 70A of the image processor 70, the image signal of the normal light image is subjected to given image processing (normal light image processing) suitable for the normal light image, and the normal light image signal is outputted. Thereafter, under the control of the controller 68, the normal light image is displayed on the display unit 18 based on the normal light image signal, and the normal light image signal is stored in the storage unit 72 when necessary.

Subsequently, when the observation mode is switched (signal switching), the procedure returns to step S1 (step S3).

Figure 10:
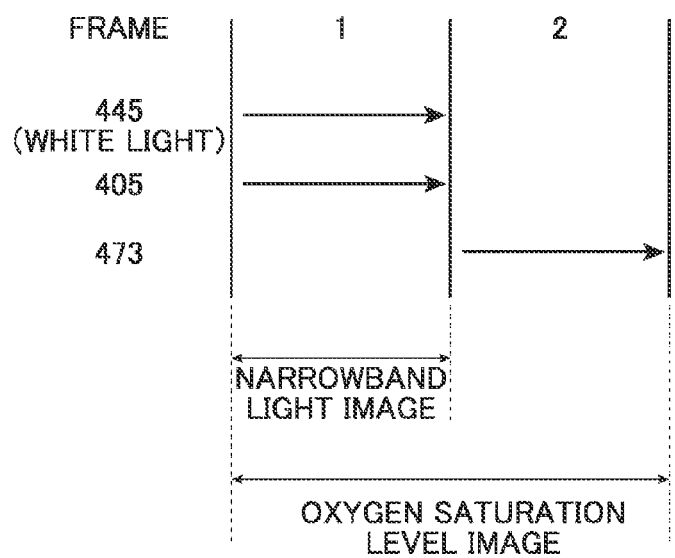
FIG. 10 is a conceptual view of an example illustrating an operation in special light observation mode in the endoscopic diagnosis system of FIG. 1.

When, on the other hand, the observation mode is judged not to be the normal light observation mode, or judged to be the special light observation mode in step S1 (NO in step S1), the narrowband light observation mode and the oxygen saturation level observation mode are alternately switched in this order in every frame time under the control of the controller 68 as illustrated in the conceptual view of FIG. 10, thereby imaging alternately a narrowband light image for blood vessel observation and a narrowband light image for oxygen saturation level observation in a time-sharing manner.

First, in the narrowband light observation mode for the first frame, the laser light sources LD1 and LD2 are turned on while the laser light source LD3 is turned off, and two channels of excitation light for normal light observation (laser beam having a central wavelength of 445 nm) and two channels of narrowband light for blood vessel observation (laser beam having a central wavelength of 405 nm) are emitted from the light source device 12 (step S4).

In the endoscope device 14, in addition to the excitation light for normal light observation, the narrowband light for blood vessel observation is guided by the optical fibers 46A, 46B, and the subject is illuminated with the white light and the narrowband light for blood vessel observation at a given emission ratio in the narrowband light observation mode. The reflected light from the subject illuminated with the white light and the narrowband light for blood vessel observation is imaged by the image sensor 58, and the A/D converter 64 outputs the image signal of the narrowband light image for blood vessel observation.

Since the ability of extracting a superficial blood vessel is determined by the light amount ratio (emission ratio) between the while light and the narrowband light for blood vessel observation, the light amount ratio therebetween is preferably 1:4 to 5 in terms of the image data ratio between the respective B channels (pixels), but is not limited thereto. When desired to display only superficial blood vessels only, it is also possible to calculate a thickness of a superficial blood vessel on the image in accordance with the magnification of the superficial blood vessel, and to carry out the frequency separation processing to particularly extract such blood vessels having the calculated thickness.

Similarly, in the processor 16, the image signal of the narrowband light image for blood vessel observation is inputted to the narrowband light image processor 70B in accordance with the observation mode, the image signal of the narrowband light image for blood vessel observation is subjected to given image processing (narrowband light image processing) suitable for the narrowband light image for blood vessel observation, and the narrowband light image signal for blood vessel observation is outputted. The narrowband light image signal for blood vessel observation is stored in the storage unit 72 under the control of the controller 68.

In the narrowband light observation mode, blood vessels lying in the superficial to intermediate layer of the subject can be observed by illuminating the subject with the laser beam having a central wavelength of 405 nm and the white light at a given emission ratio.

Then, in the oxygen saturation level observation mode for the second frame, the laser light sources LD1 and LD2 are turned off, while the laser light source LD3 is turned on, and two channels of narrowband light for oxygen saturation level observation (laser beam having a central wavelength of 473 nm) are emitted from the light source device 12 (step S5).

In the endoscope device 14, the narrowband light for oxygen saturation level observation is guided by the optical fibers 46A, 46B to illuminate the subject in the oxygen saturation level observation mode. The reflected light from the subject illuminated with the narrowband light for oxygen saturation level observation is imaged by the image sensor 58, and the A/D converter 64 outputs the image signal of the narrowband light image for oxygen saturation level observation.

Similarly, in the processor 16, the image signal of the narrowband light image for oxygen saturation level observation is inputted to the oxygen saturation level image processor 70C in accordance with the observation mode, and the image signal of the narrowband light image for oxygen saturation level observation is subjected to given image processing (oxygen saturation level image processing) suitable for the narrowband light image for oxygen saturation level observation to be described later.

That is, for the oxygen saturation level image processing, first, the signal ratio calculator 76 specifies the blood vessel region based on the narrowband light image signal for blood vessel observation in the first frame stored in the storage unit 72 and the image signal of the narrowband light image for oxygen saturation level observation in the second frame, and calculates the signal ratios B/G and R/G based on the image signal B of the B pixel in the narrowband light image for oxygen saturation level observation and the image signals G, R of the G pixel and R pixel in the narrowband light image for blood vessel observation for the pixels at the same position within the blood vessel region.

Then, the blood volume-oxygen saturation level calculator 80 calculates information on the blood volume and oxygen saturation level corresponding to the signal ratios B/G and R/G according to the correlation LUT stored in the correlation storage unit 72.

Calculation of an oxygen saturation level requires image signals corresponding to the reflected light in two wavelength ranges where the absorbance coefficient varies depending on the oxygen saturation level of blood hemoglobin and an image signal corresponding to the reflected light in a wavelength range where the absorbance coefficient does not vary.

In the oxygen saturation level observation mode according to this embodiment, by illuminating with the laser beam having a central wavelength of 473 nm, the image signal corresponding to the reflected light in a wavelength range where the absorbance coefficient varies depending on the oxygen saturation level of blood hemoglobin is obtained.

Accordingly, in order to obtain another image signal corresponding to the reflected light in a wavelength range where the absorbance coefficient varies depending on the oxygen saturation level of blood hemoglobin and an image signal corresponding to the reflected light in a wavelength range where the absorbance coefficient does not vary, one or two additional frame-time is normally required. Essentially, two to three frame-time is necessary for obtaining the narrowband light image for oxygen saturation level observation.

On the contrary, by undergoing the narrowband light observation mode and the oxygen saturation level observation mode alternately in this order as described above, the image signal of the narrowband light image for blood vessel observation acquired in the narrowband light observation mode can be used to calculate the oxygen saturation level. Hence, the endoscopic image required to calculate the oxygen saturation level can be obtained by only acquiring the narrowband light image for oxygen saturation level observation. In this manner, the accuracy of a motion picture can be improved when observing a plurality of endoscopic images at a time.

Subsequently, the oxygen saturation level image generator 82 specifies color information corresponding to the oxygen saturation level for every pixel of the blood vessel region based on the selected color table, thereby outputting a narrowband light image signal for oxygen saturation level observation. As illustrated in FIG. 6, an oxygen saturation level image is displayed as densities corresponding to the oxygen saturation level from 0 to 100% according to the LUT, where the B/G represents an oxygen saturation level and the R/G represents a blood concentration.

The controller 68 then causes the storage unit 72 to store the narrowband light image signal for oxygen saturation level observation.

Moreover, the image synthesizer 84, following the observation mode and the image display mode, combines the narrowband light image for blood vessel observation and the oxygen saturation level image based on the narrowband light image signal for blood vessel observation and the narrowband light image signal for oxygen saturation level observation stored in the storage unit 72, thereby generating a synthesized image signal where both the images are superposed or laid out.

Then, according to the observation mode and the image display mode, the controller 68 causes the display unit 18 to display the synthesized image corresponding to the synthesized image signal and the storage unit 72 to store the synthesized image signal, when necessary.

Subsequently, once the observation mode is switched from one to another in step S7, the procedure returns to step S1.

In the endoscopic diagnosis system 10, since a narrowband light image for blood vessel observation and a narrowband light image for oxygen saturation level observation are acquired simultaneously in a time-sharing manner, a narrowband light image for blood vessel observation and an oxygen saturation level image can be superposed or laid out to be simultaneously displayed as the endoscopic image in the same region under observation. At this time, while an image of superficial blood vessels is extracted in the narrowband light image for blood vessel observation, the oxygen saturation level image includes information on a superficial to an intermediate layer because a laser beam having a central wavelength of 473 nm was used for the oxygen saturation level image. Therefore, by displaying both images as being superposed, arrangement of superficial blood vessels can be also seen in the oxygen saturation level image.

Regarding the process of superposing images, for example, superficial blood vessels including new blood vessels can be extracted in the narrowband light image for blood vessel observation because the new blood vessels which are often found in a tumor lesion lie in a superficial layer, and the oxygen saturation level of the new blood vessels can be easily recognized as a result of superposing with the oxygen saturation level image.

In the narrowband light observation mode, a normal light image can be substantially acquired by reducing the emission amount of the laser beam having a central wavelength of 405 nm emitted from the laser light source LD1 to a level at which there is only ignorable effect on the narrowband light image for blood vessel observation. In this case, the light source controller 22 controls white light and the laser beam having a central wavelength of 405 nm so as to switch between a first illumination mode to illuminate the subject at the first emission ratio to acquire a narrowband light image for blood vessel observation and a second illumination mode to illuminate the subject at the second emission ratio to acquire a normal light image in which the emission amount of the laser beam having a central wavelength of 405 nm is reduced.

Figure 11:
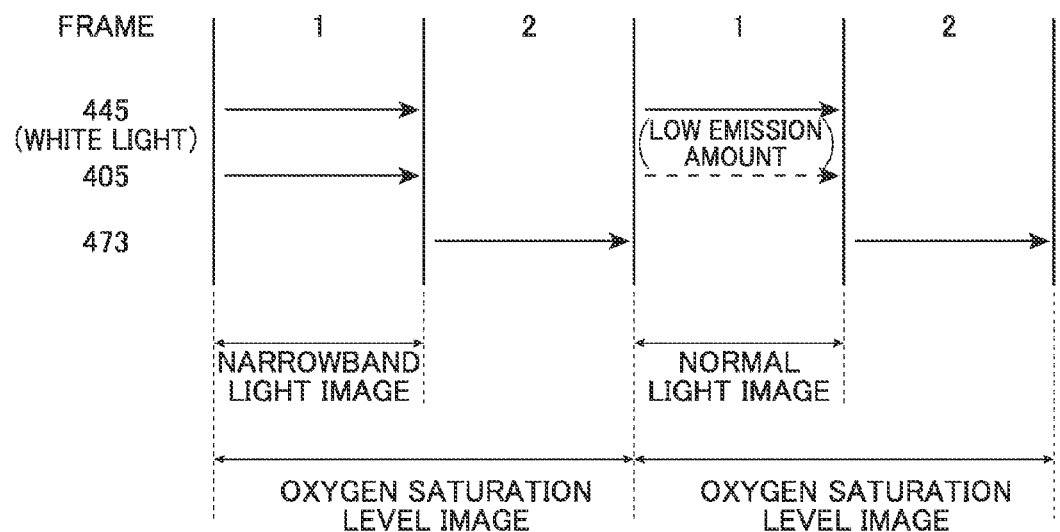
FIG. 11 is a conceptual view of an example illustrating an operation in special light observation mode in the endoscopic diagnosis system of FIG. 1.

As illustrated in the conceptual view of FIG. 11, having two-frame time as a unitary set, in the first set (in the first illumination mode), the narrowband light observation mode and the oxygen saturation level observation mode are alternately switched to one another in this order for every frame time, and in the second set (in the second illumination mode), the normal light observation mode and the oxygen saturation level observation mode are alternately switched to one another in this order for every frame time. In this way, during the narrowband light observation mode, a narrowband light image for blood vessel observation can be acquired in the first illumination mode, while a normal light image can be acquired in the second illumination mode, and even in the special light observation mode, a normal light image, a narrowband light image for blood vessel observation and an oxygen saturation level image can be simultaneously acquired in a time-sharing manner.

Figure 12:
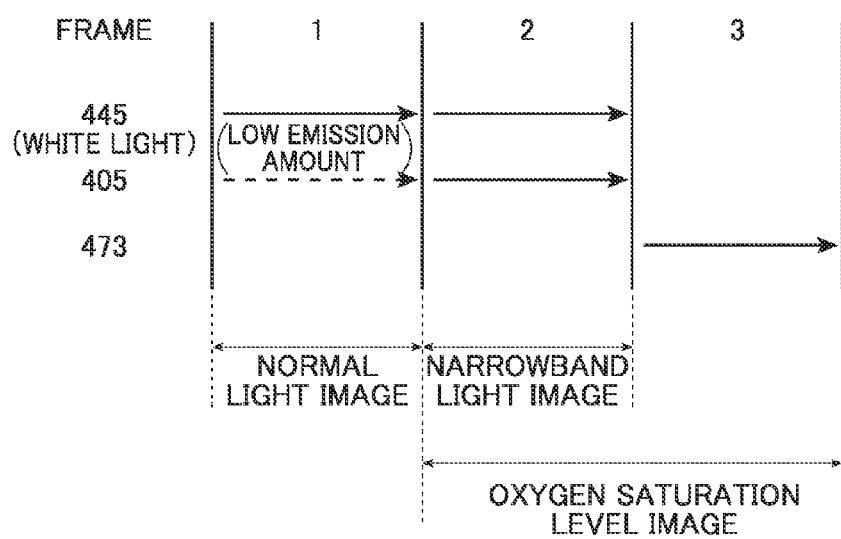
FIG. 12 is a conceptual view of an example illustrating an operation in special light observation mode in the endoscopic diagnosis system of FIG. 1.
Figure 13:
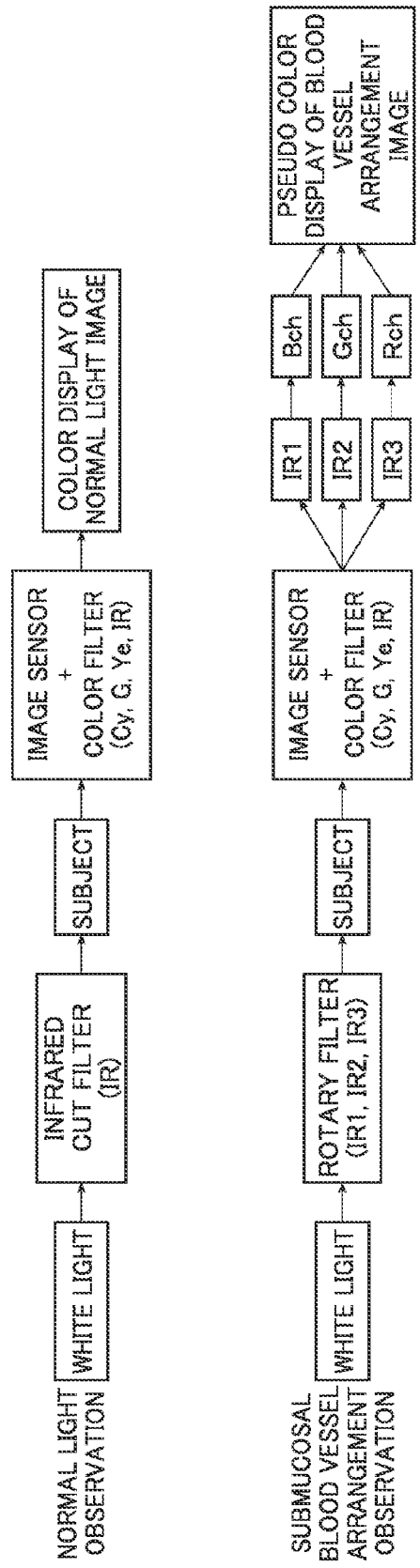
FIG. 13 is a conceptual view of an example illustrating processing performed by a conventional endoscopic diagnosis system in respective observation modes.
Figure 14:
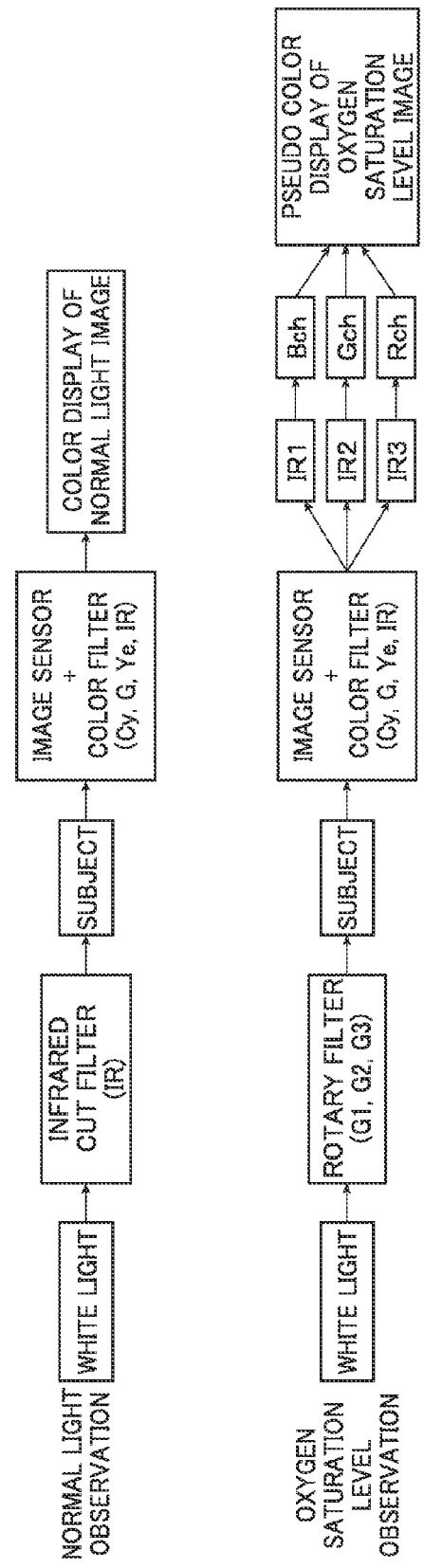
FIG. 14 is a conceptual view of an example illustrating processing performed by a conventional endoscopic diagnosis system in respective observation modes.

As illustrated in the conceptual view of FIG. 12, having three-frame time as a unitary set, the similar effect can be achieved by sequentially switching the normal light observation mode, the narrowband light observation mode and the oxygen saturation level observation mode in this order for every frame.

In addition, when a normal light image is acquired as described above in the narrowband light observation mode, for example, a synthesized image in which a normal light image, a narrowband light image for blood vessel observation and an oxygen saturation level image are superposed may be displayed, or a normal light image and a synthesized image in which a narrowband light image for blood vessel observation and an oxygen saturation level image are superposed may be displayed side by side. Moreover, a normal light image, a narrowband light image for blood vessel observation and an oxygen saturation level image may be laid out and displayed.

The present invention is basically as described above. While the invention has been described above in detail, the invention is by no means limited to the above embodiments, and various improvements and modifications may of course be made without departing from the spirit of the present invention.

What is claimed is:

1. An endoscopic diagnosis system, comprising:
   a white light source for emitting white light;
   a first narrowband light source for emitting first narrowband light which is light having a first central wavelength and has a portion of a wavelength range within a wavelength range of the white light;
   a second narrowband light source for emitting second narrowband light which is light having a second central wavelength different from the first central wavelength and has a portion of a wavelength range within the wavelength range of the white light;
   a light source controller for controlling on-off actions and light amounts of the white light source, the first narrowband light source and the second narrowband light source, respectively;
   an image sensor for receiving reflected light from a subject illuminated with the white light to acquire a normal light image in a normal light observation mode, receiving reflected light from the subject illuminated with the white light and the first narrowband light emitted at a first emission ratio toward the subject to acquire a narrowband light image for blood vessel observation in a narrowband light observation mode, and receiving reflected light from the subject illuminated with the second narrowband light emitted toward the subject to acquire a narrowband light image for oxygen saturation level observation in an oxygen saturation level observation mode;
   a controller for switching between the narrowband light observation mode and the oxygen saturation level observation mode alternately in this order to control such that the narrowband light image for blood vessel observation and the narrowband light image for oxygen saturation level observation are acquired alternately in a time-sharing manner;
   an image processor for specifying a blood vessel region from image signals of the narrowband light image for oxygen saturation level observation, obtaining an oxygen saturation level of blood hemoglobin of the subject from signal ratios of the image signals for a pixel at a same position within the blood vessel region and from a look-up table regarding a correlation of the oxygen saturation level with the signal ratios, based on the image signals of the narrowband light image for blood vessel observation and the narrowband light image for oxygen saturation level observation to generate an oxygen saturation level image showing a distribution of the oxygen saturation level; and
   a display unit for simultaneously displaying the narrowband light image for blood vessel observation and the oxygen saturation level image.

2. The endoscopic diagnosis system according to claim 1, wherein, in the narrowband light observation mode, the image processor is adapted to generate a synthesized image in which the narrowband light image for blood vessel observation and the oxygen saturation level observation image are superposed, and
   the display unit is adapted to display the synthesized image.

3. The endoscopic diagnosis system according to claim 1, wherein, in the narrowband light observation mode, the image processor is adapted to generate a synthesized image in which the narrowband light image for blood vessel observation and the oxygen saturation level image are laid out, and
   the display unit is adapted to display the synthesized image.

4. The endoscopic diagnosis system according to claim 1, wherein the light source controller is adapted to control such that, a first illumination mode and a second illumination mode are switched alternately in the narrowband light observation mode, the white light and the first narrowband light being emitted to illuminate the subject at the first emission ratio in the first illumination mode, and the first narrowband light being emitted to illuminate the subject at the second emission ratio at which an emission amount of the first narrowband light is so reduced that an effect of the first narrowband light on the narrowband light image for blood vessel observation is ignorable in the second illumination mode, and
   the image sensor is adapted to acquire the narrowband light image for blood vessel observation in the first illumination mode and the normal light image in the second illumination mode alternately in the narrowband light observation mode.

5. The endoscopic diagnosis system according to claim 4, wherein, in the narrowband light observation mode, the image processor is adapted to generate a synthesized image in which the normal light image, the narrowband light image for blood vessel observation and the oxygen saturation level image are superposed, and
   the display unit is adapted to display the synthesized image.

6. The endoscopic diagnosis system according to claim 4, wherein, in the narrowband light observation mode, the image processor is adapted to generate a synthesized image in which the narrowband light image for blood vessel observation and the oxygen saturation level image are superposed, and
   the display unit is adapted to display the normal light image and the synthesized image as being laid out.

7. The endoscopic diagnosis system according to claim 4, wherein, in the narrowband light observation mode, the image processor is adapted to generate a synthesized image in which the normal light image, the narrowband light image for blood vessel observation and the oxygen saturation level image are laid out, and
   the display unit is adapted to display the synthesized image.

8. The endoscopic diagnosis system according to claim 1, wherein the first narrowband light has a wavelength range of 405 nm±10 nm, and the second narrowband light has a wavelength range of 473 nm±10 nm.

9. The endoscopic diagnosis system according to claim 1, wherein the white light source comprises a third narrowband light source for emitting third narrowband light which is light having a third central wavelength different from the first central wavelength and the second central wavelength and has a portion of a wavelength range within the wavelength range of the white light and a fluorescent body which is excited to emit luminescent light when illuminated with the third narrowband light, so that the third narrowband light is combined with the luminescent light to generate pseudo white light.

10. The endoscopic diagnosis system according to claim 9, wherein the third narrowband light has a wavelength range of 445 nm±10 nm.

11. The endoscopic diagnosis system according to claim 1, further comprising:
   a signal ratio calculator for specifying the blood vessel region from the image signals of the narrowband light image for oxygen saturation level observation based on a difference between an image signal of a blood vessel portion and an image signal of other portion.

12. The endoscopic diagnosis system according to claim 11, wherein the signal ratio calculator obtains signal ratios B/G and R/G from image signals G and R respectively of a G channel and a R channel of the narrowband light image for blood vessel observation and from an image signal B of a B channel of the narrowband light image for oxygen saturation level observation for the pixel at the same position within the blood vessel region.

13. The endoscopic diagnosis system according to claim 12, further comprising a correlation storage unit for storing the correlation of a blood volume and the oxygen saturation level with the signal ratios B/G and R/G in a form of the look-up table.

14. The endoscopic diagnosis system according to claim 13, further comprising a blood volume-oxygen saturation level calculator for calculating the blood volume and the oxygen saturation level corresponding to the signal ratios B/G and R/G based on the correlation.

15. The endoscopic diagnosis system according to claim 14, further comprising
   an oxygen saturation level image generator, and
   wherein the oxygen saturation level image generator has a color table in which color information is assigned depending on magnitude of the oxygen saturation level, and specifies the color information corresponding to the oxygen saturation level calculated in the blood volume-oxygen saturation level calculator by using the color table to generate a narrowband light image signal for oxygen saturation level observation reflecting the oxygen saturation level of blood hemoglobin.

* * * * *